United States Patent
Nishiwaki et al.

(10) Patent No.: US 6,875,880 B2
(45) Date of Patent: Apr. 5, 2005

(54) SILYLATION OF HYDROXYL GROUPS

(75) Inventors: Hiromi Nishiwaki, Niigata-ken (JP); Ayumu Kiyomori, Niigata-ken (JP); Tohru Kubota, Niigata-ken (JP)

(73) Assignee: Shin-Etsu Chemical, Co., Ltd., Tokyo (JP)

( * ) Notice: Subject to any disclaimer, the term of this patent is extended or adjusted under 35 U.S.C. 154(b) by 239 days.

(21) Appl. No.: 10/347,308

(22) Filed: Jan. 21, 2003

(65) Prior Publication Data

US 2003/0139619 A1 Jul. 24, 2003

(30) Foreign Application Priority Data

Jan. 21, 2002 (JP) .......................... 2002-011443
May 8, 2002 (JP) .......................... 2002-132660

(51) Int. Cl.[7] .................. C07F 7/21; C07F 7/08
(52) U.S. Cl. ........................ 556/440; 556/460
(58) Field of Search .................. 556/440, 560

(56) References Cited

PUBLICATIONS

Sprung et al., The Reaction of Some Silanols and Siloxanes with n–Octyl Alcohol, J. Am. Chem. Soc., 26, 1961, pp. 552–557.*
Grubb, A Rate Study of the Silanol Condensation Reaction at 25 C in Alcoholic Solvent, J. Am. Chem. Soc., 76, 1954, pp. 3408–3414.*
Greene et al, Protective Groups in Organic Synthesis, Third Edition, 1999, pp. 113–148, 237–241, 273–276, and 428–431.
C.C. Sweeley et al, J.Am. Chem. Soc., 1963, vol. 85, pp. 2497–2507.
Stallings, David L. et al, Biochemical And Biophysical Research Communications, vol. 31, No. 4, 1968, pp. 616–622.
W. Verboom et al, Synthesis, 1981, pp. 807–809.
Ojima, Iwao et al, Chemistry Letters, 1973, pp. 501–504.
Blackwell, James M. et al, J. Org. Chem, 1999, vol. 64, pp. 4887–4892.
Tanabe, Yoo et al, Tetrahedron Letters, 1994, vol. 35, No. 45, pp. 8413–8414.
Clive, Derrick L. J. et al, Tetrahedron Letters, 1991, vol. 32, No. 49, pp. 7159–7160.
Gilman, M.: Journal of the American Chemical Society, vol. 73, 1951, pp. 2367–2368, XP002236523.
Database Crossfire Beilstein 'Online! Accession No. 5223064 (reaction ID) XP002236526 (abstract only).
Sprung, M.M et al.: Journal of Organic Chemistry, vol. 26, 1961, pp. 552–557, XP002236524.
Boehm, T.: Journal of Organic Chemistry, vol. 61, 1996, pp. 6498–6499, XP002236525.

* cited by examiner

*Primary Examiner*—Johann R. Richter
*Assistant Examiner*—Chukwuma Nwaonicha
(74) *Attorney, Agent, or Firm*—Birch, Stewart, Kolasch & Birch, LLP

(57) ABSTRACT

A compound having a non-silanol hydroxyl group and a compound having a silanol group are subjected to dehydrative condensation in the presence of a compound of formula (1), (2) or (3):

$$MX_n \quad (1)$$

$$Z_a SiR^1_b R^2_c R^3_d \quad (2)$$

$$C_m F_{2m+1} SO_3 Y \quad (3)$$

wherein M is a metal, n is the valence of metal M, and X is halogen or $C_m F_{2m+1} SO_3$; a=1 to 4, b, c and d=0 to 3, a+b+c+d=4, $R^1$, $R^2$ and $R^3$ are monovalent hydrocarbon groups, Z is halogen or $C_m F_{2m+1} SO_3$; Y is H or HW, W is an amine $NR^4 R^5 R^6$ or a nitrogen-containing heterocyclic compound, $R^4$, $R^5$ and $R^6$ are H or monovalent hydrocarbyl groups, and m=0 to 10. The method is effective in silylating the hydroxyl group without generating a substantial amount of harmful by-products such as hydrogen chloride or triethylamine hydrochloride.

5 Claims, No Drawings

SILYLATION OF HYDROXYL GROUPS

TECHNICAL FIELD

This invention relates to a method for silylating hydroxyl groups for the preparation of silyl ethers or silyl esters which are widely used in industry as intermediates to pharmaceuticals, agrochemicals, and so forth.

BACKGROUND OF THE INVENTION

Protection of protic functional groups by silylation has become a well-established tool in organic synthesis. Silyl ethers or silyl esters are derivatives of corresponding alcohols and carboxylic acids whose hydroxyl group has been silylated, and they are widely used as intermediates to pharmaceuticals, agrochemicals, and so forth.

A typical process for the silylation of hydroxyl groups employs compounds having a silicon-chlorine bond within the molecule, that is, chlorosilanes as silylating agents. See Greene and Wuts, Protective Groups in Organic Synthesis, Third Edition, John Wiley & Sons, New York, 1999, pp. 113–148, 237–241, 273–276, 428–431 and the references cited therein. By reacting a chlorosilane and a compound having a non-silanol hydroxyl group, the hydroxyl group is silylated to produce a silyl ether or a silyl ester.

However, the process using chlorosilanes has a number of drawbacks. First, the reaction is a dehydrochlorinative condensation in which a stoichiometric amount of highly toxic hydrogen chloride is produced as a by-product with the progress of silylating reaction. The reaction equilibrates at a certain stage, thus cannot be driven to completion unless the hydrogen chloride is removed. Therefore, the process using chlorosilanes requires that the silylating reaction be conducted typically in the presence of bases such as triethylamine, which makes the reaction not cost-effective. Moreover, as a consequence, this process entails a formation of a crystalline salt such as triethylamine hydrochloride, and thus needs a step of removing the salt from the reaction mixture. Finally, the hydrochloride salt of a substantial amount should be disposed as a waste, which also makes the process less viable.

Among silylating processes which do not form hydrogen chloride, hexamethyldisilazane is most commonly used as a silylating agent (see J. Am. Chem. Soc., 1963, Vol. 85, page 2497–2507). Nevertheless, this process still suffers from generation of toxic ammonia as a by-product. It is also possible to carry out silylation using commercially available various silylating agents such as N,O-bis(trimethylsilyl)-trifluoroacetamide and N,N'-bis(trimethylsilyl)urea (see Biochem. Biophys. Res. Commun., 1968, Vol. 31, page 616–622, and Synthesis, 1981, page 807–809). However, large amounts of by-products originating from the silylating agents are produced, which necessitates the step of removing the by-products and isolating the desired compound.

It is also known to use hydrosilanes as silylating agents and subject alcohols to dehydrogenation reaction therewith for silylation. This process carries out reaction in the presence of catalysts such as palladium on activated carbon, transition metal complexes, tris(pentafluorophenyl)-borane, tetrabutylammonium fluoride and the like (see Chem. Lett., 1973, page 501–504, J. Org. Chem., 1999, Vol. 64, page 4887–4892, Tetrahedron Lett., 1994, Vol. 35, page 8413–8414). The by-product is hydrogen gas, which provides the advantage that the step of separating the silylated compound and the by-product is eliminated. However, it comes with a serious disadvantage, the increase in the risk of potential explosion, especially when practiced on a large scale, because hydrogen gas has a wide range of explosion.

On the other hand, it was reported to use tert-butyldimethylsilanol as a silylating agent (see Tetrahedron Lett., 1991, page 7159–7160). In this process, an alcohol and the silanol are subjected to a formal dehydrative condensation under Mitsunobu reaction conditions, but an expensive reagent must be used and large amounts of by-products are formed therefrom.

To solve the aforementioned problems, there is a need to have a method for preparing silyl ethers or silyl esters without forming a substantial amount of harmful by-products such as hydrogen chloride or triethylamine hydrochloride.

SUMMARY OF THE INVENTION

The present invention addresses these concerns and its object is to provide a method of subjecting a compound having a non-silanol hydroxyl group and a compound having a silanol group to dehydrative condensation reaction for silylating the compound having a non-silanol hydroxyl group without forming a substantial amount of harmful by-products such as hydrogen chloride or triethylamine hydrochloride, whereby a silyl ether or a silyl ester is produced.

It has been found that dehydrative condensation reaction between a compound having a non-silanol hydroxyl group and a compound having a silanol group can effectively take place using a compound of the following general formula (1), (2) or (3) as a catalyst.

According to the invention, there is provided a method for silylating a hydroxyl group, comprising subjecting a compound having a non-silanol hydroxyl group and a compound having a silanol group to dehydrative condensation in the presence of a compound of the following general formula (1), (2) or (3).

$$MX_n \quad (1)$$

Herein M is a metal having a valence of at least 1, n is an integer equal to the valence of metal M, and X is a halogen or a fluorinated sulfonate represented by $C_mF_{2m+1}SO_3$ wherein m is an integer of 0 to 10. M is typically a metal of Group 3 to 15.

$$Z_aSiR^1_bR^2_cR^3_d \quad (2)$$

Herein a is an integer of 1 to 4, b, c and d each are an integer of 0 to 3, satisfying a+b+c+d=4, each of $R^1$, $R^2$ and $R^3$ which may be the same or different is a substituted or unsubstituted monovalent hydrocarbyl group of 1 to 20 carbon atoms, Z is a halogen or a fluorinated sulfonate represented by $C_mF_{2m+1}SO_3$ wherein m is an integer of 0 to 10.

$$C_mF_{2m+1}SO_3Y \quad (3)$$

Herein Y is hydrogen or a cation represented by HW, W is an amine represented by $NR^4R^5R^6$ or a substituted or unsubstituted, nitrogen-containing heterocyclic compound of 1 to 20 carbon atoms, $R^4$, $R^5$ and $R^6$ each are hydrogen or a substituted or unsubstituted monovalent hydrocarbyl group of 1 to 20 carbon atoms, and m is an integer of 0 to 10.

In one preferred embodiment, a compound having the general formula (4a) or (5a) and the compound having a silanol group are subjected to dehydrative condensation in the presence of a compound of the general formula (1) or (2), thereby forming a silyl ether or a silyl ester.

$$R^{7a}\text{—OH} \tag{4a}$$

$$R^{7a}\text{—COOH} \tag{5a}$$

Herein $R^{7a}$ is a substituted or unsubstituted, monovalent hydrocarbyl group, free of aliphatic unsaturation, of 1 to 20 carbon atoms.

In another preferred embodiment, a compound having the general formula (4) or (5) and a compound having a silanol group are subjected to dehydrative condensation in the presence of a compound of the general formula (3), thereby forming a silyl ether or a silyl ester.

$$R^7\text{—OH} \tag{4}$$

$$R^7\text{—COOH} \tag{5}$$

Herein $R^7$ is a substituted or unsubstituted monovalent hydrocarbyl group of 1 to 20 carbon atoms.

The compound having a silanol group is preferably a compound of the following general formula (6) or (7).

$$R^8R^9R^{10}\text{Si—OH} \tag{6}$$

$$\text{HO—(SiR}^{11}\text{R}^{12}\text{O—)}_L R^{13} \tag{7}$$

Herein each of $R^8$, $R^9$ and $R^{10}$ which may be the same or different is a substituted or unsubstituted monovalent hydrocarbyl group of 1 to 20 carbon atoms or a hydroxyl group; each of $R^{11}$ and $R^{12}$ which may be the same or different is a substituted or unsubstituted monovalent hydrocarbyl group of 1 to 20 carbon atoms or a hydroxyl group, $R^{13}$ is hydrogen or a substituted or unsubstituted monovalent hydrocarbyl group of 1 to 20 carbon atoms, and L is an integer of at least 2.

DESCRIPTION OF THE PREFERRED EMBODIMENTS

The compound having a non-silanol hydroxyl group used herein is a compound having at least one hydroxyl group (excluding the hydroxyl group of a silanol group) in the molecule, for example, an alcoholic hydroxyl group or phenolic OH group, and includes saturated or unsaturated aliphatic alcohols, aromatic alcohols, phenols, and carboxylic acids. The compound may have substituents.

Preferred compounds having a non-silanol hydroxyl group are compounds of the general formula (4) or (5):

$$R^7\text{—OH} \tag{4}$$

$$R^7\text{—COOH} \tag{5}$$

wherein $R^7$ is a substituted or unsubstituted monovalent hydrocarbyl group of 1 to 20 carbon atoms. Examples of $R^7$ include straight, branched and cyclic alkyl groups such as methyl, ethyl, n-propyl, isopropyl, n-butyl, isobutyl, tert-butyl, pentyl, cyclopentyl, hexyl, cyclohexyl, octyl, decyl, dodecyl and stearyl; straight, branched and cyclic alkenyl groups such as vinyl, allyl, propenyl, butenyl, hexenyl, cyclohexenyl, decenyl and undecenyl; straight, branched and cyclic alkynyl groups such as ethynyl, propynyl and butynyl; aryl groups such as phenyl, tolyl, xylyl, naphthyl and biphenyl; aralkyl groups such as benzyl, phenylethyl and phenylpropyl; and substituted ones of the foregoing in which some or all of the hydrogen atoms are substituted with halogen atoms (e.g., fluoro, chloro or bromo), cyano, amino, alkylamino, nitro, acetoxy, acyloxy, carboxyl, amide, acetamide groups, or organoxy groups such as alkoxy, alkenyloxy and aryloxy.

Also included are compounds of formula (4) wherein some or all of the hydrogen atoms on the group $R^7$ are substituted with hydroxyl or carboxyl groups, that is, diols, triols, hydroxycarboxylic acids and the like; and compounds of formula (5) wherein some or all of the hydrogen atoms on the group $R^7$ are substituted with carboxyl or hydroxyl groups, that is, dicarboxylic acids, tricarboxylic acids, hydroxycarboxylic acids and the like.

Illustrative of suitable aliphatic alcohols are methanol, ethanol, ethylene glycol, 1-propanol, 2-propanol, 1,2-propanediol, crotyl alcohol, cyclobutanol, 3-buten-1-ol, 3-buten-2-ol, 2-butene-1,4-diol, 1-butanol, 2-butanol, 2-methyl-1-propanol, 2-methyl-2-propanol, cyclobutanol, 1-pentanol, 2-pentanol, 3-pentanol, 1-methylcyclopropanemethanol, 2-methylcyclopropanemethanol, amyl alcohol, cyclohexanol, hexyl alcohol, 2-hexanol, 3-hexanol, 1-heptanol, 2-heptanol, cyclohexylmethanol, 1-octanol, 2-octanol, 1-nonanol, 2-nonanol, 9-decen-1-ol, 1-decanol, 1-undecanol, 2-undecanol, 10-undecen-1-ol, 1-dodecanol, 2-dodecanol, 2-butyloctanol, 1-tridecanol, dicyclohexylmethanol, 1-pentadecanol, 1-hexadecanol, 2-hexadecanol, 1-heptadecanol, 1-octadecanol, 1-nonadecanol, 1-eicosanol, 2-octyl-1-dodecanol, 2-ethoxyethanol, diethoxymethanol, 2-butoxyethanol, 3-benzyloxy-1-propanol, 2-dimethylaminoethanol, 1-diethylamino-2-propanol, 3-diethylamino-2-propanol, 1-dimethylamino-2-propanol, 3-nitro-2-pentanol, glycolonitrile, 3-hydroxypropionitrile, 4-chloro-1-butanol, 3-bromo-2,2-dimethyl-1-propanol, 3-chloro-2,2-dimethyl-1-propanol, 6-chloro-1-hexanol, 6-bromo-1-hexanol, and 1-fluoro-2-octanol.

Examples of suitable aromatic alcohols include benzyl alcohol, β-phenylethyl alcohol, methylphenylcarbinol, cinnamyl alcohol, phthalyl alcohol, 1,1-diphenylethanol, 2,2-diphenylethanol, and cyclopropyldiphenylmethanol.

Examples of suitable phenols include phenol, hydroquinone, p-cresol, m-cresol, o-cresol, 2-ethylphenol, 3-ethylphenol, 4-ethylphenol, 2-allylphenol, 4-methoxyphenol, 2-nitrophenol, 3-nitrophenol, 2-acetamidophenol, 3-acetamidophenol, and 4-acetamidophenol.

Illustrative of suitable carboxylic acids are acetic acid, acrylic acid, propionic acid, methacrylic acid, crotonic acid, cyclopropanecarboxylic acid, butyric acid, isobutyric acid, 4-pentynoic acid, 3,3'-dimethylacrylic acid, 2-pentenoic acid, 4-pentenoic acid, α-methylcrotonic acid, 2-methylbutyric acid, trimethylacetic acid, valeric acid, 1-cyclopentene-1-carboxylic acid, 3-cyclopentene-1-carboxylic acid, cyclopentanecarboxylic acid, 2-methyl-2-pentenoic acid, tert-butylacetic acid, 2,2-dimethylbutyric acid, 2-ethylbutyric acid, hexanoic acid, benzoic acid, 2-cyclopentene-1-acetic acid, cyclohexanecarboxylic acid, cyclopentylacetic acid, 2,2-dimethyl-4-pentenoic acid, 6-heptenoic acid, phenylacetic acid, o-toluic acid, m-toluic acid, p-toluic acid, 2-octynoic acid, 2-ethylhexanoic acid, octanoic acid, phenylpropionic acid, cinnamic acid, hydrocinnamic acid, 2-phenylpropionic acid, o-tolylacetic acid, m-tolylacetic acid, p-tolylacetic acid, 2-norbornaneacetic acid, cyclohexanepropionic acid, nonanoic acid, 4-isopropylbenzoic acid, α-methylhydrocinnamic acid, 2-methylhydrocinnamic acid, 2-phenylbutyric acid, 3-phenylbutyric acid, 4-phenylbutyric acid, 4-propylbenzoic acid, 3-(p-tolyl)-propionic acid, 2,4,6-trimethylbenzoic acid, 3-noradamantanecarboxylic acid, cyclohexanebutyric acid, decanoic acid, 1-naphthoic acid, 2-naphthoic acid, 4-butylbenzoic acid, 4-tert-butylbenzoic acid, 5-phenylvaleric acid, 10-undecenoic acid, 4-butylcyclohexane-carboxylic acid, cyclohexanevaleric acid, undecanoic acid, maleic acid, trifluoroacetic acid, pivalic acid, L-lactic acid, glycolic acid, lauric acid, tridecanoic acid, tridecanoic diacid, myristic acid, palmitic acid, heptadecanoic acid, stearic acid, eicosanoic acid, and heneicosanoic acid.

The compound having a silanol group used herein is selected from classes of substances such as, for example, triorganosilanols, diorganosilane diols, and siloxanes having at least one hydroxyl group attached to a silicon atom. Preferred compounds having a silanol group are those of the following general formulae (6) and (7).

$$R^8R^9R^{10}Si\text{—}OH \quad (6)$$

$$HO\text{—}(SiR^{11}R^{12}O\text{—})_LR^{13} \quad (7)$$

Herein each of $R^8$, $R^9$, $R^{10}$, $R^{11}$ and $R^{12}$ which may be the same or different is a substituted or unsubstituted monovalent hydrocarbyl group of 1 to 20 carbon atoms or a hydroxyl group. The monovalent hydrocarbyl groups represented by $R^8$ to $R^{12}$ are as exemplified for $R^7$. $R^{13}$ is hydrogen or a substituted or unsubstituted monovalent hydrocarbyl group of 1 to 20 carbon atoms. The monovalent hydrocarbyl groups represented by $R^{13}$ are as exemplified for $R^7$. L is an integer of at least 2, preferably an integer of 2 to 1,000.

Examples of triorganosilanols suitable as the compound having a silanol group include trimethylsilanol, triethylsilanol, tripropylsilanol, triisopropylsilanol, tributylsilanol, triisobutylsilanol, tripentylsilanol, trihexylsilanol, triheptylsilanol, trioctylsilanol, trinonylsilanol, tridecylsilanol, triundecylsilanol, tridodecylsilanol, tritridecylsilanol, tritetradecylsilanol, tripentadecylsilanol, trihexadecylsilanol, triheptadecylsilanol, trioctadecylsilanol, trinonadecylsilanol, trieicosylsilanol, tert-butyldimethylsilanol, thexyldimethylsilanol, pentyldiisopropylsilanol, hexyldiisopropylsilanol, heptyldiisopropylsilanol, octyldiisopropylsilanol, nonyldiisopropylsilanol, decyldiisopropylsilanol, undecyldiisopropylsilanol, dodecyldiisopropylsilanol, tridecyldiisopropylsilanol, pentadecyldiisopropylsilanol, nonadecyldiisopropylsilanol, eicosyldiisopropylsilanol, octyldimethylsilanol, methyldiphenylsilanol, cyclopropyldimethylsilanol, cyclohexyldimethylsilanol, cyclopentyldimethylsilanol, octadecyldimethylsilanol, phenyldimethylsilanol, triphenylsilanol, 4-chlorophenyldimethylsilanol, 1,4-bis(hydroxydimethylsilyl)benzene, 3-chloropropyldiisopropylsilanol, 3-chloropropyldimethylsilanol, 3-methacryloxypropyldimethylsilanol, 3,3,3-trifluoropropyldiisopropylsilanol, and 3,3,3-trifluoropropyldimethylsilanol.

Examples of suitable diorganosilane diols include dimethylsilane diol, diphenylsilane diol and di-tert-butylsilane diol.

Examples of siloxanes having at least one hydroxyl group attached to a silicon atom include 1,1,3,3-tetramethyldisiloxane-1,3-diol, 1,1,3,3-tetraisopropyldisiloxane-1,3-diol, 1,1,3,3-tetraphenyldisiloxane-1,3-diol, 1,3-dimethyl-1,3-diphenyldisiloxane-1,3-diol, 1,1,3,3,3-pentamethyldisiloxan-1-ol, 1,1,3,3,3-pentaphenyldisiloxan-1-ol, 1,1,3,3,5,5-hexamethyltrisiloxane-1,5-diol, 1,1,3,3,5,5-hexaphenyltrisiloxane-1,5-diol, 1,3,5-trimethyl-1,3,5-triphenyltrisiloxane-1,5-diol, 1,1,3,3,5,5,5-heptamethyltrisiloxan-1-ol, 1,1,3,3,5,5,5-heptaphenyltrisiloxan-1-ol, α,ω-dihydroxypolydimethylsiloxane, α,ω-dihydroxypolydiphenylsiloxane, and α,ω-dihydroxypolymethylphenylsiloxane.

The amount of the silanol group-bearing compound used is not critical. Preferably the silanol group-bearing compound is used in such amounts as to provide 0.5 to 5 moles, more preferably 0.8 to 2 moles of silicon-bonded hydroxyl groups on the silanol group-bearing compound per mole of hydroxyl groups on the non-silanol hydroxyl group-bearing compound.

The compound used as the catalyst in the method of the invention has the general formula (1), (2) or (3).

$$MX_n \quad (1)$$

Herein M is a metal having a valence of at least 1, n is an integer equal to the valence of metal M, and X is a halogen or a fluorinated sulfonate represented by $C_mF_{2m+1}SO_3$ wherein m is an integer of 0 to 10.

$$Z_aSiR^1_bR^2_cR^3_d \quad (2)$$

Herein a is an integer of 1 to 4, b, c and d each are an integer of 0 to 3, satisfying a+b+c+d=4, each of $R^1$, $R^2$ and $R^3$ which may be the same or different is a substituted or unsubstituted monovalent hydrocarbon group of 1 to 20 carbon atoms, Z is a halogen or a fluorinated sulfonate represented by $C_mF_{2m+1}SO_3$ wherein m is an integer of 0 to 10.

$$C_mF_{2m+1}SO_3Y \quad (3)$$

Herein Y is hydrogen or a cation represented by HW wherein W is an amine represented by $NR^4R^5R^6$ or a substituted or unsubstituted, nitrogen-containing heterocyclic compound of 1 to 20 carbon atoms, $R^4$, $R^5$ and $R^6$ each are hydrogen or a substituted or unsubstituted monovalent hydrocarbyl group of 1 to 20 carbon atoms, and m is an integer of 0 to 10.

In formula (1), the metal is preferably selected from metals of Groups 3 to 15 including Sc, Y, Ti, Hf, Ru, Cu, Ag, Hg, Al, In, La, Ce, Pr, Nd, Sm, Gd, Tb, Dy, Ho, Er, Tm, Yb, Ge, Sn, Pb, Sb and Bi.

Examples of the compound of formula (1) include titanium chloride, aluminum chloride, samarium fluoride, ytterbium fluoride, samarium chloride, indium chloride, ytterbium chloride, samarium bromide, indium bromide, samarium iodide, aluminum trifluoromethanesulfonate, cerium trifluoromethanesulfonate, copper trifluoromethanesulfonate, dysprosium trifluoromethanesulfonate, erbium trifluoromethanesulfonate, gadolinium trifluoromethanesulfonate, hafnium trifluoromethanesulfonate, holmium trifluoromethanesulfonate, indium trifluoromethanesulfonate, lanthanum trifluoromethanesulfonate, ruthenium trifluoromethanesulfonate, mercury trifluoromethanesulfonate, neodymium trifluoromethanesulfonate, praseodymium trifluoromethanesulfonate, samarium trifluoromethanesulfonate, scandium trifluoromethanesulfonate, silver trifluoromethanesulfonate, terbium trifluoromethanesulfonate, thulium trifluoromethanesulfonate, ytterbium trifluoromethanesulfonate, yttrium trifluoromethanesulfonate, zinc trifluoromethanesulfonate, tin trifluoromethanesulfonate, germanium trifluoromethanesulfonate, palladium trifluoromethanesulfonate, bismuth trifluoromethanesulfonate, antimony trifluoromethanesulfonate, indium fluorosulfonate, indium pentafluoroethanesulfonate, indium heptafluoropropanesulfonate, indium nonafluorobutanesulfonate, indium undecafluoropentanesulfonate, indium tridecafluorohexanesulfonate, indium pentadecafluoroheptanesulfonate, indium heptadecafluorooctanesulfonate, indium nonadecafluorononanesulfonate, and indium heneicosafluorodecanesulfonate.

In formula (2), $R^1$, $R^2$ and $R^3$ are each independently selected from substituted or unsubstituted monovalent hydrocarbyl groups of 1 to 20 carbon atoms, examples of which are as set forth for $R^7$.

Examples of the compound of formula (2) wherein Z is halogen include fluorosilanes such as trimethylfluorosilane, triethylfluorosilane, triisopropylfluorosilane, and t-butyldimethylfluorosilane; chlorosilanes such as trimethylchlorosilane, triethylchlorosilane, triisopropylchlorosilane, and t-butyldimethylchlorosilane; bromosilanes such as trimethylbromosilane, triethylbromosilane, triisopropylbromosilane, and t-butyldimethylbromosilane; and iodosilanes such as trimethyliodosilane, triethyliodosilane, triisopropyliodosilane, and t-butyldimethyliodosilane.

Examples of the compound of formula (2) wherein Z is fluorinated sulfonate include trimethylsilyl trifluoromethanesulfonate, triethylsilyl trifluoromethanesulfonate, triisobutylsilyl trifluoromethanesulfonate, t-butyldimethylsilyl trifluoromethanesulfonate, truisopropylsilyl trifluoromethanesulfonate, thexyldimethylsilyl trifluoromethanesulfonate, hexyldimethylsilyl trifluoromethanesulfonate, octyldimethylsilyl trifluoromethanesulfonate, nonyldimethylsilyl trifluoromethanesulfonate, decyldimethylsilyl trifluoromethanesulfonate, undecyldimethylsilyl trifluoromethanesulfonate, dodecyldimethylsilyl trifluoromethanesulfonate, tridecyldimethylsilyl trifluoromethanesulfonate, pentadecyldimethylsilyl trifluoromethanesulfonate, nonadecyldimethylsilyl trifluoromethanesulfonate, eicosyldimethylsilyl trifluoromethanesulfonate, cyclopropyldimethylsilyl trifluoromethanesulfonate, cyclohexyldimethylsilyl trifluoromethanesulfonate, cyclopentyldimethylsilyl trifluoromethanesulfonate, phenyldimethylsilyl trifluoromethanesulfonate, triphenylsilyl trifluoromethanesulfonate, 3,3,3-trifluoropropyldimethylsilyl trifluoromethanesulfonate, trimethylsilyl fluorosulfonate, triethylsilyl fluorosulfonate, t-butyldimethylsilyl fluorosulfonate, triisopropylsilyl fluorosulfonate, trimethylsilyl pentafluoroethanesulfonate, triethylsilyl pentafluoroethanesulfonate, t-butyldimethylsilyl pentafluoroethanesulfonate, triisopropylsilyl pentafluoroethanesulfonate, trimethylsilyl heptafluoropropanesulfonate, triethylsilyl heptafluoropropanesulfonate, t-butyldimethylsilyl heptafluoropropanesulfonate, triisopropylsilyl heptafluoropropanesulfonate, trimethylsilyl nonafluorobutanesulfonate, triethylsilyl nonafluorobutanesulfonate, t-butyldimethylsilyl nonafluorobutanesulfonate, triisopropylsilyl nonafluorobutanesulfonate, trimethylsilyl undecafluoropentanesulfonate, triethylsilyl undecafluoropentanesulfonate, t-butyldimethylsilyl undecafluoropentanesulfonate, triisopropylsilyl undecafluoropentanesulfonate, trimethylsilyl tridecafluorohexanesulfonate, triethylsilyl tridecafluorohexanesulfonate, t-butyldimethylsilyl tridecafluorohexanesulfonate, triisoprepylsilyl tridecafluorohexanesulfonate, trimethylsilyl pentadecafluoroheptanesulfonate, triethylsilyl pentadecafluoroheptanesulfonate, t-butyldimethylsilyl pentadecafluoroheptanesulfonate, triisopropylsilyl pentadecafluoroheptanesulfonate, trimethylsilyl heptadecafluorooctanesulfonate, triethylsilyl heptadecafluorooctanesulfonate, t-butyldimethylsilyl heptadecafluorooctanesulfonate, triisopropylsilyl heptadecafluorooctanesulfonate, trimethylsilyl nonadecafluorononanesulfonate, triethylsilyl nonadecafluorononanesulfonate, t-butyldimethylsilyl nonadecafluorononanesulfonate, triisopropylsilyl nonadecafluorononanesulfonate, trimethylsilyl heneicosafluorodecanesulfonate, triethylsilyl heneicosafluorodecanesulfonate, t-butyldimethylsilyl heneicosafluorodecanesulfonate, and triisopropylsilyl heneicosafluorodecanesulfonate.

In formula (3), examples of the monovalent hydrocarbyl groups represented by $R^4$, $R^5$ and $R^6$ are as set forth for $R^7$. The letter m is an integer of 0 to 10.

Examples of the fluorinated sulfonic acid include fluorosulfonic acid, trifluoromethanesulfonic acid, pentafluoroethanesulfonic acid, heptafluoropropanesulfonic acid, nonafluorobutanesulfonic acid, undecafluoropentanesulfonic acid, tridecafluorohexanesulfonic acid, pentadecafluoroheptanesulfonic acid, heptadecafluorooctanesulfonic acid, nonadecafluorononanesulfonic acid, and heneicosafluorodecanesulfonic acid.

Suitable salts of fluorinated sulfonic acids include salts of the foregoing fluorinated sulfonic acids with amine or nitrogen-containing heterocyclic compounds.

Examples of these amine or nitrogen-containing heterocyclic compounds include methylamine, ethylamine, propylamine, isopropylamine, butylamine, tert-butylamine, amylamine, hexylamine, heptylamine, octylamine, nonylamine, decylamine, undecylamine, dodecylamine, tridecylamine, tetradecylamine, pentadecylamine, cetylamine, dimethylamine, diethylamine, dipropylamine, diisopropylamine, dibutylamine, diamylamine, dicyclohexylamine, trimethylamine, triethylamine, tripropylamine, tributylamine, triamylamine, trioctylamine, diisopropylethylamine, allylamine, diallylamine, triallylamine, cyclopropylamine, cyclobutylamine, cyclopentylamine, cyclohexylamine, aniline, methylaniline, dimethylaniline, ethylaniline, diethylaniline, o-toluidine, m-toluidine, p-toluidine, benzylamine, dibenzylamine, tribenzylamine, diphenylamine, triphenylamine, α-naphthylamine, β-naphthylamine, piperidine, piperazine, pyrrolidine, pyrrole, pyridine, imidazole, indole, quinoline, acridine, triazole, tetrazole, morpholine, N-methylmorpholine, 2,6-dimethylpyridine, 2,6-dimethylpeperidine, 4-dimethylaminopyridine, 2,2,6,6-tetramethylpiperidine, 2,5-dimethylpiperazine, 1,5-diazabicyclo[4.3.0]-5-nonene, 1,4-diazabicyclo[2.2.2]octane, 1,8-diazabicyclo[5.4.0]-7-undecene, ethylenediamine, N,N,N',N'-tetramethylethylenediamine, N,N,N'-trimethylethylenediamine, diethylenetriamine, stearylamine, tetrakis(dimethylamino)ethylene, p-chloroaniline, and p-bromoaniline.

It is not critical how the salt of fluorinated sulfonic acid be present in a reactor. For example, a fluorinated sulfonic acid and an amine or nitrogenous heterocyclic compound are admitted into the reactor whereupon the salt of fluorinated sulfonic acid is generated in situ in the reactor. Alternatively, a fluorinated sulfonic acid and an amine or nitrogenous heterocyclic compound are previously mixed to form the salt of fluorinated sulfonic acid before it is fed into the reactor.

In the practice of the invention, a compound having a non-silanol hydroxyl group and a compound having a silanol group are subjected to dehydrative condensation in the presence of a compound of formula (1), (2) or (3). Particularly when a compound of formula (1) or (2) is used, the compound having a non-silanol hydroxyl group is preferably selected from among those compounds free of aliphatic unsaturation, specifically compounds of formulae (4) and (5) wherein $R^7$ is an aliphatic unsaturation-free group, that is, compounds having the general formulae (4a) and (5a):

$$R^{7a}—OH \quad (4a)$$

$$R^{7a}—COOH \quad (5a)$$

wherein $R^{7a}$ is a substituted or unsubstituted, aliphatic unsaturation-free monovalent hydrocarbon group of 1 to 20 carbon atoms.

The amount of the compound of formula (1) to (3) used is not critical, but is preferably in the range of 0.1 to 0.0001 mole, especially 0.1 to 0.001 mole per mole of hydroxyl groups on the non-silanol hydroxyl group-bearing compound. Less than 0.0001 mole of the compound of formula (1) to (3) may fail to provide the desired catalytic effect whereas more than 0.1 mole leads to a possibility that more by-products be formed, resulting in a reduced yield of the silylated compound.

In the practice of the invention, the temperature for silylation reaction is generally −70° C. to 200° C., and preferably −20° C. to 150° C. The reaction atmosphere is preferably an inert atmosphere such as nitrogen although reaction can proceed in an air atmosphere. The pressure under which reaction is conducted is preferably atmospheric pressure or a reduced pressure, though not critical.

The reaction is generally carried out in solution form with a solvent added although the reaction can take place even in a solventless system. Useful solvents for the reaction are, for example, aromatic hydrocarbon solvents such as benzene, toluene and xylene, ether solvents such as diethyl ether and tetrahydrofuran, aliphatic hydrocarbon solvents such as hexane, and aprotic polar solvents such as dimethylformamide, N-methylpyrrolidone, acetonitrile, halogenated hydrocarbon solvents such as dichloromethane, chloroform, 1,2-dichloroethane, chlorobenzene.

During the reaction, water forms, which should preferably be removed from the reaction solution although the reaction can take place without interference even when the water formed is not removed. The water can be removed by any desired means, for example, by (azeotropic) distillation or by employing a dehydrating agent. Examples of the dehydrating agent used herein include anhydrous inorganic salts such as anhydrous magnesium sulfate, anhydrous sodium sulfate and anhydrous calcium chloride, carbodiimides such as N,N'-dicyclohexylcarbodiimide, silica gel, and molecular sieves.

By the method for silylating hydroxyl groups according to the invention, the desired silylated compound results from dehydrative condensation between the hydroxyl group on the non-silanol hydroxyl group-bearing compound and the hydroxyl group of silanol group on the silanol group-bearing compound. The desired compound may be represented by the formula:

$$R^7—O—SiR^8R^9R^{10}$$

for the combination of the compounds of formulae (4) and (6);

$$R^7—COO—SiR^8R^9R^{10}$$

for the combination of the compounds of formulae (5) and (6);

$$R^7—O—(SiR^{11}R^{12}O—)_mR^{13}$$

for the combination of the compounds of formulae (4) and (7); and $$R^7—COO—(SiR^{11}R^{12}O—)_mR^{13}$$

for the combination of the compounds of formulae (5) and (7).

In the event where $R^7$ further has a non-silanol hydroxyl group or carboxyl group, the desired compound results from dehydrative condensation between the hydroxyl group of $R^7$ and the hydroxyl group of silanol group, though it varies depending on the molar ratio of the compounds of formulae (4) and (6), (5) and (6), (4) and (7), or (5) and (7) used in reaction.

In the event where any one of $R^8$, $R^9$, $R^{10}$, $R^{11}$ and $R^{12}$ is a hydroxyl group and $R^{13}$ is hydrogen, the desired compound results from dehydrative condensation among the hydroxyl group of any one of $R^8$, $R^9$, $R^{10}$, $R^{11}$ and $R^{12}$, the terminal hydroxyl group formed when $R^{13}$ is hydrogen, and the non-silanol hydroxyl group, though it varies depending on the molar ratio of the compounds of formulae (4) and (6), (5) and (6), (4) and (7), or (5) and (7) used in reaction.

EXAMPLE

Examples of the invention are given below by way of illustration and not by way of limitation.

Example 1

A 100-ml four-necked flask equipped with a Dimroth condenser, stirrer, thermometer and Dean-Stark trap was thoroughly purged with nitrogen and then charged with 60 ml of toluene, 6.6 g ($5.0 \times 10^{-2}$ mol) of t-butyldimethylsilanol, 7.9 g ($5.0 \times 10^{-2}$ mol) of 1-decanol, and 0.31 g ($5.0 \times 10^{-4}$ mol) of ytterbium (III) trifluoromethanesulfonate. With a nitrogen flow to the outlet of the condenser kept, the flask was heated to effect toluene reflux. The toluene reflux was kept for two hours while the water formed during reaction was distilled off together with toluene. At the end of reaction, the reaction solution was cooled to room temperature. Composition analysis by gas chromatography revealed that 1-decanol had been silylated at 95.6% conversion.

Example 2

Reaction was carried out as in Example 1 aside from using 8.6 g ($6.5 \times 10^{-2}$ mol) of t-butyldimethylsilanol instead of 6.6 g ($5.0 \times 10^{-2}$ mol) of t-butyldimethylsilanol. At the end of reaction, the product was analyzed for composition by gas chromatography, finding that 1-decanol had been silylated at 99.2% conversion.

Example 3

Reaction was carried out as in Example 1 aside from using 6.6 g ($5.0 \times 10^{-2}$ mol) of triethylsilanol instead of 6.6 g ($5.0 \times 10^{-2}$ mol) of t-butyldimethylsilanol. At the end of reaction, the product was analyzed for composition by gas chromatography, finding that 1-decanol had been silylated at 94.1% conversion.

Example 4

A 100-ml four-necked flask equipped with a Dimroth condenser, stirrer and thermometer was thoroughly purged with nitrogen and then charged with 60 ml of toluene, 6.6 g ($5.0 \times 10^{-2}$ mol) of triethylsilanol, 7.9 g ($5.0 \times 10^{-2}$ mol) of 1-decanol, and 0.31 g ($5.0 \times 10^{-4}$ mol) of ytterbium (III) trifluoromethanesulfonate. With a nitrogen flow to the outlet of the condenser kept, the flask contents were heated at 100° C. The flask was kept at the temperature for two hours, then cooled to room temperature. Composition analysis by gas chromatography revealed that 1-decanol had been silylated at 80.8% conversion.

Example 5

Reaction was carried out as in Example 1 aside from using 0.28 g ($5.0 \times 10^{-4}$ mol) of indium (III) trifluoromethanesulfonate instead of 0.31 g ($5.0 \times 10^{-4}$ mol) of ytterbium (III) trifluoromethanesulfonate. At the end of reaction, the product was analyzed for composition by gas chromatography, finding that 1-decanol had been silylated at 92.7% conversion.

Example 6

Reaction was carried out as in Example 1 aside from using 0.25 g ($5.0 \times 10^{-4}$ mol) of scandium (III) trifluoromethanesulfonate instead of 0.31 g ($5.0 \times 10^{-4}$ mol) of ytterbium (III) trifluoromethanesulfonate. At the end of reaction, the product was analyzed for composition by gas chromatography, finding that 1-decanol had been silylated at 93.1% conversion.

Example 7

Reaction was carried out as in Example 1 aside from using 0.18 g ($5.0 \times 10^{-4}$ mol) of copper (II) trifluoromethanesulfonate instead of 0.31 g ($5.0 \times 10^{-4}$ mol) of ytterbium (III) trifluoromethanesulfonate. At the end of reaction, the product was analyzed for composition by gas chromatography, finding that 1-decanol had been silylated at 71.4% conversion.

Example 8

Reaction was carried out as in Example 1 aside from using 0.11 g ($5.0 \times 10^{-4}$ mol) of copper (I) trifluoromethanesulfonate instead of 0.31 g ($5.0 \times 10^{-4}$ mol) of ytterbium (III) trifluoromethanesulfonate. At the end of reaction, the product was analyzed for composition by gas chromatography, finding that 1-decanol had been silylated at 86.9% conversion.

Example 9

Reaction was carried out as in Example 1 aside from using 6.5 g ($5.0 \times 10^{-2}$ mol) of 2-octanol instead of 7.9 g ($5.0 \times 10^{-2}$ mol) of 1-decanol. At the end of reaction, the product was analyzed for composition by gas chromatography, finding that 2-octanol had been silylated at 84.2% conversion.

Example 10

Reaction was carried out as in Example 1 aside from using 8.5 g ($5.0 \times 10^{-2}$ mol) of 10-undecen-1-ol instead of 7.9 g ($5.0 \times 10^{-2}$ mol) of 1-decanol. At the end of reaction, the product was analyzed for composition by gas chromatography, finding that 10-undecen-1-ol had been silylated at 92.6% conversion.

Example 11

Reaction was carried out as in Example 4 aside from using 13.8 g ($5.0 \times 10^{-2}$ mol) of triphenylsilanol instead of 6.6 g ($5.0 \times 10^{-2}$ mol) of triethylsilanol and 2.3 g ($5.0 \times 10^{-2}$ mol) of ethanol instead of 7.9 g ($5.0 \times 10^{-2}$ mol) of 1-decanol. At the end of reaction, the product was analyzed for composition by gas chromatography, finding that ethanol had been silylated at 70.5% conversion.

Example 12

A 100-ml four-necked flask equipped with a Dimroth condenser, stirrer, thermometer and Dean-Stark trap was thoroughly purged with nitrogen and then charged with 60 ml of toluene, 6.6 g ($5.0 \times 10^{-2}$ mol) of t-butyldimethylsilanol, 7.9 g ($5.0 \times 10^{-2}$ mol) of 1-decanol, and 0.13 g ($5.0 \times 10^{-4}$ mol) of t-butyldimethylsilyl trifluoromethanesulfonate. The contents were stirred for 5 minutes at about 22° C. At the end of stirring, the reaction solution was analyzed for composition by gas chromatography, finding that 1-decanol had been silylated at 90.3% conversion.

Example 13

Reaction was carried out as in Example 12 aside from using 6.6 g ($5.0 \times 10^{-2}$ mol) of triethylsilanol instead of 6.6 g ($5.0 \times 10^{-2}$ mol) of t-butyldimethylsilanol and 0.15 g ($5.0 \times 10^{-4}$ mol) of triisopropylsilyl trifluoromethanesulfonate instead of 0.13 g ($5.0 \times 10^{-4}$ mol) of t-butyldimethylsilyl trifluoromethanesulfonate. At the end of reaction, the product was analyzed for composition by gas chromatography, finding that 1-decanol had been silylated at 96.3% conversion.

Example 14

A 100-ml four-necked flask equipped with a Dimroth condenser, stirrer and thermometer was thoroughly purged with nitrogen and then charged with 60 ml of toluene, 8.7 g ($5.0 \times 10^{-2}$ mol) of triisopropylsilanol, 7.9 g ($5.0 \times 10^{-2}$ mol) of 1-decanol, and 0.075 g ($5.0 \times 10^{-4}$ mol) of trifluoromethanesulfonic acid. With a nitrogen flow to the outlet of the condenser kept, the flask contents were heated at 100° C. The flask was kept at the temperature for two hours, then cooled to room temperature. Composition analysis by gas chromatography revealed that 1-decanol had been silylated at 73.2% conversion.

Example 15

A 100-ml four-necked flask equipped with a Dimroth condenser, stirrer, thermometer and measuring water trap was thoroughly purged with nitrogen and then charged with 60 ml of toluene, 8.7 g ($5.0 \times 10^{-2}$ mol) of triisopropylsilanol, 7.9 g ($5.0 \times 10^{-2}$ mol) of 1-decanol, and 0.075 g ($5.0 \times 10^{-4}$ mol) of trifluoromethanesulfonic acid. With a nitrogen flow to the outlet of the condenser kept, the flask was heated to effect toluene reflux. The toluene reflux was kept for two hours while the water formed during reaction was distilled off together with toluene. At the end of reaction, the reaction solution was cooled to room temperature. Composition analysis by gas chromatography revealed that 1-decanol had been silylated at 92.3% conversion.

Example 16

A 100-ml four-necked flask equipped with a Dimroth condenser, stirrer and thermometer was thoroughly purged with nitrogen and then charged with 8.7 g ($5.0 \times 10^{-2}$ mol) of triisopropylsilanol, 7.9 g ($5.0 \times 10^{-2}$ mol) of 1-decanol, and 0.075 g ($5.0 \times 10^{-4}$ mol) of trifluoromethanesulfonic acid. With a nitrogen flow to the outlet of the condenser kept, the flask contents were heated at 100° C. The flask was kept at the temperature for two hours, then cooled to room temperature. Composition analysis by gas chromatography revealed that 1-decanol had been silylated at 77.9% conversion.

Example 17

Reaction was carried out as in Example 15 aside from using 6.6 g ($5.0 \times 10^{-2}$ mol) of tert-butyldimethylsilanol instead of 8.7 g ($5.0 \times 10^{-2}$ mol) of triisopropylsilanol. At the end of reaction, the product was analyzed for composition by gas chromatography, finding that 1-decanol had been silylated at 87.4% conversion.

Example 18

Reaction was carried out as in Example 15 aside from using 6.5 g ($5.0 \times 10^{-2}$ mol) of 2-octanol instead of 7.9 g ($5.0 \times 10^{-2}$ mol) of 1-decanol. At the end of reaction, the product was analyzed for composition by gas chromatography, finding that 2-octanol had been silylated at 69.9% conversion.

Example 19

Reaction was carried out as in Example 15 aside from using 5.0 g ($5.0 \times 10^{-2}$ mol) of phenol instead of 7.9 g ($5.0 \times 10^{-2}$ mol) of 1-decanol. At the end of reaction, the product was analyzed for composition by gas chromatography, finding that phenol had been silylated at 84.4% conversion.

Example 20

Reaction was carried out as in Example 15 aside from using 8.5 g ($5.0 \times 10^{-2}$ mol) of 10-undecen-1-ol instead of 7.9 g ($5.0 \times 10^{-2}$ mol) of 1-decanol. At the end of reaction, the product was analyzed for composition by gas chromatography, finding that 10-undecen-1-ol had been silylated at 97.7% conversion.

Example 21

Reaction was carried out as in Example 14 aside from using 13.8 g ($5.0 \times 10^{-2}$ mol) of triphenylsilanol instead of 8.7 g ($5.0 \times 10^{-2}$ mol) of triisopropylsilanol and 2.3 g ($5.0 \times 10^{-2}$ mol) of ethanol instead of 7.9 g ($5.0 \times 10^{-2}$ mol) of 1-decanol. At the end of reaction, the product was analyzed for composition by gas chromatography, finding that ethanol had been silylated at 77.0% conversion.

Example 22

Reaction was carried out as in Example 15 aside from using 5.8 g ($5.0 \times 10^{-2}$ mol) of hexanoic acid instead of 7.9 g ($5.0 \times 10^{-2}$ mol) of 1-decanol. At the end of reaction, the product was analyzed for composition by gas chromatography, finding that hexanoic acid had been silylated at 92.2% conversion.

Example 23

Reaction was carried out as in Example 15 aside from using 4.3 g ($5.0 \times 10^{-2}$ mol) of methacrylic acid instead of 7.9 g ($5.0 \times 10^{-2}$ mol) of 1-decanol. At the end of reaction, the product was analyzed for composition by gas chromatography, finding that methacrylic acid had been silylated at 71.7% conversion.

Example 24

Reaction was carried out as in Example 15 aside from using 6.6 g ($5.0 \times 10^{-2}$ mol) of triethylsilanol instead of 8.7 g ($5.0 \times 10^{-2}$ mol) of triisopropylsilanol. At the end of reaction, the product was cooled to room temperature and analyzed for composition by gas chromatography, finding that triethylsilanol had been completely consumed and 1-decanol had been silylated at 48.1% conversion. Hexaethyldisiloxane was produced as a by-product, with a ratio of silyl ether to hexaethyldisiloxane produced being 1:0.66.

Example 25

Reaction was carried out as in Example 24 aside from feeding 0.051 g ($5.0 \times 10^{-4}$ mol) of diisopropylamine subsequent to the trifluoromethanesulfonic acid. At the end of reaction, the product was cooled to room temperature and analyzed for composition by gas chromatography, finding that triethylsilanol had been completely consumed and 1-decanol had been silylated at 90.0% conversion. Hexaethyldisiloxane was produced as a by-product, with a ratio of silyl ether to hexaethyldisiloxane produced being 1:0.039.

Example 26

A 100-ml four-necked flask equipped with a Dimroth condenser, stirrer and thermometer was thoroughly purged with nitrogen and then charged with 60 ml of toluene, 0.075 g ($5.0 \times 10^{-4}$ mol) of trifluoromethanesulfonic acid, 0.076 g ($5.0 \times 10^{-4}$ mol) of 1,8-diazabicyclo[5.4.0]-7-undecene, and 5.1 g ($5.0 \times 10^{-2}$ mol) of 1-hexanol, which were stirred. Further, 4.15 g ($2.5 \times 10^{-2}$ mol) of 1,1,3,3-tetramethyldisiloxane-1,3-diol was admitted into the reactor, which was evacuated to a reduced pressure of 4.7 kPa and heated at 35° C. The reactor was kept at the temperature for two hours and resumed atmospheric pressure. Composition analysis by gas chromatography revealed that 1,1,3,3-tetramethyldisiloxane-1,3-diol had completely reacted, and 1,3-dihexyloxy-1,1,3,3-tetramethyldisiloxane was produced at a selectivity of 79.1%. By-products included 1,5-dihexyloxy-1,1,3,3,5,5-hexamethyltrisiloxane and 1,7-dihexyloxy-1,1,3,3,5,5,7,7-octamethyltetrasiloxane.

Example 27

A 100-ml four-necked flask equipped with a Dimroth condenser, stirrer and thermometer was thoroughly purged with nitrogen and then charged with 60 ml of toluene, 8.7 g ($5.0 \times 10^{-2}$ mol) of triisopropylsilanol, 3.6 g ($5.0 \times 10^{-2}$ mol) of acrylic acid, and 0.15 g ($1.0 \times 10^{-3}$ mol) of trifluoromethanesulfonic acid. The reactor was evacuated to a reduced pressure of 4.7 kPa and heated at 35° C. The reactor was kept at the temperature for two hours and resumed atmospheric pressure. Composition analysis by gas chromatography revealed that acrylic acid had been silylated at a reaction rate of 75.2%.

According to the invention, effective dehydration and condensation reaction takes place between a non-silanol hydroxyl group-bearing compound and a silanol group-bearing compound for silylating the hydroxyl group without generating harmful by-products such as hydrogen chloride or triethylamine hydrochloride.

Japanese Patent Application Nos. 2002-011443 and 2002-132660 are incorporated herein by reference.

Although some preferred embodiments have been described, many modifications and variations may be made thereto in light of the above teachings. It is therefore to be understood that the invention may be practiced otherwise than as specifically described without departing from the scope of the appended claims.

What is claimed is:

1. A method for silylating a hydroxyl group, comprising subjecting a compound having a non-silanol hydroxyl group and a compound having a silanol group to dehydrative condensation in the presence of a compound of the following general formula (1), (2) or (3):

$$MX_n \quad (1)$$

wherein M is a metal having a valence of at least 1, n is an integer equal to the valence of metal M, and X is a halogen or a fluorinated sulfonate represented by $C_mF_{2m+1}SO_3$ wherein m is an integer of 0 to 10, $$Z_aSiR^1_bR^2_cR^3_d \quad (2)$$

wherein a is an integer of 1 to 4, b, c and d each are an integer of 0 to 3, satisfying a+b+c+d=4, each of $R^1$, $R^2$ and $R^3$ which may be the same or different is a substituted or unsubstituted monovalent hydrocarbyl group of 1 to 20 carbon atoms, Z is a halogen or a fluorinated sulfonate represented by $C_mF_{2m+1}SO_3$ wherein m is an integer of 0 to 10, $$C_mF_{2m+1}SO_3Y \quad (3)$$

wherein Y is hydrogen or a cation represented by HW, W is an amine represented by $NR^4R^5R^6$ or a substituted or unsubstituted, nitrogen-containing heterocyclic compound of 1 to 20 carbon atoms, $R^4$, $R^5$ and $R^6$ each are hydrogen or a substituted or unsubstituted monovalent hydrocarbyl group of 1 to 20 carbon atoms, and m is an integer of 0 to 10.

2. The method of claim 1 wherein a compound having the general formula (4a) or (5a):

$$R^{7a}\text{—OH} \quad (4a)$$

$$R^{7a}\text{—COOH} \quad (5a)$$

wherein $R^{7a}$ is a substituted or unsubstituted, monovalent hydrocarbyl group, free of aliphatic unsaturation, of 1 to 20 carbon atoms and the compound having a silanol group are subjected to dehydrative condensation in the presence of a compound of the general formula (1) or (2), thereby forming a silyl ether or a silyl ester.

3. The method of claim 1 wherein in formula (1), M is a metal of Group 3 to 15.

4. The method of claim 1 wherein a compound having the general formula (4) or (5):

$$R^{7a}\text{—OH} \quad (4)$$

$$R^{7a}\text{—COOH} \quad (5)$$

wherein $R^7$ is a substituted or unsubstituted monovalent hydrocarbyl group of 1 to 20 carbon atoms and a compound having a silanol group are subjected to dehydration and condensation in the presence of a compound of the general formula (3), thereby forming a silyl ether or a silyl ester.

5. The method of claim 1 wherein the compound having a silanol group has the following general formula (6) or (7):

$$R^8R^9R^{10}Si\text{—OH} \quad (6)$$

wherein each of $R^8$, $R^9$ and $R^{10}$ which may be the same or different is a substituted or unsubstituted monovalent hydrocarbyl group of 1 to 20 carbon atoms or a hydroxyl group, $$HO\text{—}(SiR^{11}R^{12}O\text{—})_LR^{13} \quad (7)$$

wherein each of $R^{11}$ and $R^{12}$ which may be the same or different is a substituted or unsubstituted monovalent hydrocarbyl group of 1 to 20 carbon atoms or a hydroxyl group, $R^{13}$ is hydrogen or a substituted or unsubstituted monovalent hydrocarbyl group of 1 to 20 carbon atoms, and L is an integer of at least 2.

* * * * *